(12) United States Patent
Kresge

(10) Patent No.: US 8,084,393 B1
(45) Date of Patent: Dec. 27, 2011

(54) POTATO TREATMENT COMPOSITION

(76) Inventor: Paul O. Kresge, Forest Lake, WA (US)

( * ) Notice: Subject to any disclaimer, the term of this patent is extended or adjusted under 35 U.S.C. 154(b) by 1360 days.

(21) Appl. No.: 11/671,999

(22) Filed: Feb. 6, 2007

Related U.S. Application Data

(60) Provisional application No. 60/765,711, filed on Feb. 6, 2006.

(51) Int. Cl.
*A01N 25/26* (2006.01)

(52) U.S. Cl. .................................................. 504/100

(58) Field of Classification Search .............. 504/100
See application file for complete search history.

(56) References Cited

U.S. PATENT DOCUMENTS

| | | | |
|---|---|---|---|
| 2,168,532 A | | 8/1939 | Mcmath et al. |
| 2,853,415 A | | 9/1958 | Douglas et al. |
| 3,059,615 A | | 10/1962 | Kuceski et al. |
| 3,286,691 A | | 11/1966 | Mcfadden |
| 3,560,194 A | | 2/1971 | Phillips et al. |
| 3,921,581 A | | 11/1975 | Brewer |
| 3,941,090 A | | 3/1976 | Fry |
| 3,983,842 A | | 10/1976 | Marion et al. |
| 4,145,206 A | | 3/1979 | Ford |
| 4,258,660 A | | 3/1981 | Pris et al. |
| 4,529,407 A | | 7/1985 | Johnston et al. |
| 4,561,860 A | | 12/1985 | Gulley et al. |
| 4,579,579 A | | 4/1986 | Kerr |
| 4,607,594 A | | 8/1986 | Thacker |
| 4,621,011 A | | 11/1986 | Fleischer et al. |
| 4,727,824 A | | 3/1988 | Ducharme et al. |
| 4,821,677 A | | 4/1989 | Harrison |
| 4,883,021 A | * | 11/1989 | Ducharme et al. ............ 119/171 |
| 4,954,517 A | | 9/1990 | Sutter et al. |
| 4,999,048 A | | 3/1991 | Freepons |
| 5,007,953 A | | 4/1991 | Chollet |
| 5,024,690 A | * | 6/1991 | Chollet ......................... 504/189 |
| 5,041,410 A | | 8/1991 | Ivie |
| 5,085,175 A | | 2/1992 | Clements, Jr. et al. |
| 5,219,818 A | | 6/1993 | Ivie |
| 5,229,348 A | | 7/1993 | Ivie |
| 5,578,622 A | * | 11/1996 | Ikeda et al. ................... 514/372 |
| 5,667,718 A | | 9/1997 | Jones et al. |
| 6,228,883 B1 | | 5/2001 | Riggs |
| 7,026,390 B2 | | 4/2006 | O'Brien-Bernini et al. |

FOREIGN PATENT DOCUMENTS

EP 447366 A1 9/1991

OTHER PUBLICATIONS

Mesh to micron conversion chart.*

* cited by examiner

*Primary Examiner* — Johann Richter
*Assistant Examiner* — Thor Nielsen
(74) *Attorney, Agent, or Firm* — Albert W. Watkins

(57) ABSTRACT

A potato treatment composition and method assists in the suberization process. In accord with the preferred embodiment, a potato treatment composition incorporates organic material, which may be derived from organic waste or residue, preferably from oilseed hulls and most preferably from ground or powdered oilseed sunflower seed hulls, into powder compositions. Incorporating organic matter having elevated oil content greatly reduces generation of fugitive dust, reduces clumping as compared to known fungicide dusts, and reduces shrinkage of potato seed pieces due to moisture depletion. The use of ground or powdered sunflower seed hulls as a carrier and/or diluent makes beneficial and productive use of an organic residue which is a byproduct of other industries.

11 Claims, No Drawings

POTATO TREATMENT COMPOSITION

CROSS REFERENCE TO RELATED APPLICATIONS

This application claims priority to U.S. provisional patent application Ser. No. 60/765,711 filed Feb. 6, 2006 herewith, entitled "Oilseed Hulls for Reducing Fugitive Dust Generation from Powdered Materials" and naming the present inventor, the contents which are incorporated herein by reference.

BACKGROUND OF THE INVENTION

1. Field of the Invention

This invention pertains generally to plant husbandry, and more particularly to methods and compositions having utility in potato treatment.

2. Description of the Related Art

Potatoes have origins that have been documented as early as 7,000 years ago. This seemingly simple crop existed for thousands of years unknown to Europeans, in the Andean region of South America. However, once the first potatoes were exported to Europe, they were rapidly and extensively adopted as a staple food crop. Some individuals claim the potato was the most valuable commodity discovered in the new world.

The extent of adoption, and the importance of farming practices, is perhaps best illustrated by the Irish potato famine which occurred in 1845 to 1849. The potato had become so vital to society, as such an abundant and low-cost staple, that there was an associated increase in population and even greater dependence upon the potato. The introduction of the disease late blight, combined with an unstable political situation, is associated with the starvation of one million Irish and the emigration of another two million. This large number of deaths and emigration is of a magnitude more frequently thought of as being associated with World Wars than with food supplies of the time period.

Today, potatoes rank fourth among all food crops in total production, behind rice, wheat, and corn. In 2002, the United States, which is the fifth-highest producer world-wide, sold forty billion pounds of potatoes for approximately 2.8 billion dollars. Consequently, potato farming practices and disease control have been and remain very vital to modern civilization. Any practices which can improve upon existing technologies are of great economic importance.

One practice which is commonly associated with potatoes is the generation of potato seed pieces prior to planting. The majority of farmers in the Western and Midwestern United States plant potato seed pieces rather than whole potatoes. A recommended practice is to select potato seed tubers weighing between 3.5 and 10 ounces. For most varieties the tubers are cut into seed pieces weighing from 1.5 to 2.5 ounces, each of which are generally capable of producing new potato plants.

When freshly cut, the potato is more susceptible to disease, since there is no skin on the cut to provide protection. While it is possible to directly plant these potatoes, without a protective skin yields will be undesirably reduced. Instead, in a process called suberization, the cut is allowed to heal prior to planting in a way which will improve yields. The healing involves the deposition of a complex fat-based compound called suberin in the outer two or three layers of intact cells. This suberin layer protects the surface from pathogens, and reduces moisture loss. Eventually a new layer called the phellem layer is developed and becomes suberized, ultimately forming a barrier comparable to the skin of the potato.

The initial suberization is competed in two to four days, but the formation of the phellem layer may require one to two weeks. Unfortunately, as already noted, until suberization is completed, the seed pieces are more vulnerable to pathogens. To prevent undesirable rot and decay during the suberization process, cutting knives and associated equipment are preferably kept in a relatively sterile condition by careful cleaning and sanitation with suitable disinfectants. However, once cut and exposed to air and airborne pathogens, the tuber surface is still vulnerable.

To reduce or prevent disease from developing in the cut tuber piece, freshly cut surfaces of the tubers are most preferably treated with fungicide dust. The dust will help to protect the tuber until a new barrier can be established by suberization. Seed pieces may be stored for 10 to 14 days while a new wound barrier tissue or phellem layer develops over the cut surface, or planted within about five days of cutting, after the initial suberization (cut-and-plant). In some cases, a liquid pesticide is sprayed on the seed pieces and then a powder is added to control excess liquid and promote drying of the surface. Application of a pesticide treatment may also be advantageous when whole, uncut, tubers are used for planting (single-drop).

The fungicidal dust can include active ingredients for preventing fungi or other opportunistic organisms including mold, insects and bacteria from negatively affecting the seed pieces prior to planting while the fresh cut seed pieces are drying and forming a barrier tissue and after planting prior to and during sprouting. Active ingredients may include insecticides, fungicides, and herbicides or other pesticides; as well as surfactants, nutrients, pigments and fertilizers; or other materials based on the intended action. Active ingredients are typically highly concentrated so they are commonly attached to a carrier and diluted with a diluent. A carrier is a substance impregnated with the active ingredient, whereas the diluent dilutes the active ingredient.

The other ingredients besides the active ingredients are sometimes referred to as 'inert ingredients' although this language is losing appeal since rarely is an ingredient completely inert. The other ingredients typically include relatively benign materials used for a "carrier" and/or a "diluent." Many powdered pesticides require that active ingredients be applied at very low rates per unit of area, but active ingredients as manufactured are highly concentrated so dilution is required from a carrier or diluent. For liquid pesticides, water is the chief diluent, but dry pesticides require other materials. A dry carrier, sometimes referred to as a dry diluent, or simply "diluent", is used with dry pesticides to dilute the active ingredient. If the active ingredient is impregnated on a carrier, then the carrier with active ingredient can be incorporated in a diluent. In some cases, the active ingredient can be incorporated directly into the diluent. The diluent and often the carrier may comprise a variety of materials, such as talc, zeolites, and wood flour, and the diluent and carrier may even be of the same composition.

Powdered materials are used in many commercial processes and products. Powder manufacturing, handling and end-use often generates undesirable airborne dust, referred to as "fugitive dust", which is a leading environmental contaminant that commonly poses health risks, particularly to those individuals employed in proximity. Background information can be found in the following articles, each which are hereby incorporated by reference:

Bohl, William H., Nora Olsen, Stephen L. Love and Phillip Nolte. 2003. Seed and Planting Management. Pp. 91-107

In Jeffrey C. Stark and Stephen L. Love, Potato Production Systems, University of Idaho Agricultural Communications. ISBN 1-58803-001-6.

Gill, Thomas E., Ted M. Zobeck, John E. Stout, and James M. Gregory. 1997. Fugitive dust generation in the laboratory. Wind Erosion: An International Symposium/Workshop. Manhattan, Kans. 3-5 June.

International Union of Pure and Applied Chemistry (IUPAC). 1990. Glossary of Atmospheric Chemistry Terms. See Calvert, Jack G. Pure and Applied Chemistry, 62(11):2167-2219.

World Health Organization. 1999. Hazard Prevention and Control in the Work Environment: Airborne Dust. WHO/SDE/OEH/99.14.

"Dust" is defined by the International Union of Pure and Applied Chemists (IUPAC, 1990) as "small, dry, solid particles projected into the air by natural forces, such as wind, volcanic eruption, and by mechanical or manmade processes such as crushing, grinding, milling, drilling, demolition, shoveling, conveying, screening, bagging and sweeping. Dust particles are usually in the size range from about 1 to 100 microns in diameter, and they settle slowly under the influence of gravity." The International Standardization Organization (ISO 4225-ISO, 1994) modifies the definition to refer to particles less than 75 microns in diameter.

The World Health Organization (WHO) notes that particle diameter does not fully explain how the particle behaves in its airborne state and defines the particle aerodynamic diameter as "the diameter of a hypothetical sphere of density 1 g/cm$^3$ having the same terminal settling velocity in calm air as the particle in question, regardless of its geometric size, shape and true density (WHO, 1999). WHO further defines the following fractions for health-related measurement. The "inhalable fraction" is hazardous when deposited anywhere in the respiratory tract. The "thoracic fraction" is hazardous when deposited anywhere within the lung airways including the gas-exchange region. And, the "respirable fraction" is hazardous when deposited anywhere in the gas-exchange region. Respirable dust is generally described as the fraction below four (4) microns. However, standard fractions are often taken at below ten microns and below two and one-half (2.5) microns.

Dry pesticides are known to release dust into the air when manufactured, handled or when applied, creating a potential health concern for manufacturers, handlers and applicators. In most cases, a person is needed to apply the pesticide but the respirable dust is a serious and undesirable health concern. Reducing airborne respirable dust is therefore highly desirable.

An example of a material that generates respirable dust is a fungicide dust used for treatment of potato seed pieces prior to planting. Commercial potato seed treatment product formulations typically include a blend of red alder (*Alnus rubra*) or Douglas fir (*Pseudotsuga menziesii*) bark, talc, and zeolite as the diluent materials or carrier. Physical properties of these materials provide acceptable adherence to moist surfaces of cut seed while avoiding coagulating or clumping which can plug application equipment.

Chollet discloses a seed treatment dust in U.S. Pat. Nos. 5,007,953 and 5,024,690, the teachings of each which are incorporated herein by reference, which comprises comminuted alder bark, a diluent material and an active ingredient. Chollet discloses using the seed treatment dust on seeds of grains, legumes, onions, tubers and flowers, and particularly, the dusting of tuber seeds such as potato seeds. However, the use of alder bark is not as efficacious as desired, due to cost, limited supply and because it does not effectively reduce fugitive dust, among other reasons.

U.S. Pat. No. 6,228,883 to Riggs, the teachings which are also incorporated herein by reference, discloses a fungicidal composition comprising a solid or liquid diluent, including carriers, such as talc, zeolites, alder bark, kaolin, diatomaceous earth, mineral oil, water, and the like. Potato seed treatments used in the Riggs' examples were based on a "potato dust inert system" (PDIS) shown in the present Table 1, where three ingredients, talc, zeolite and alder bark comprise 100% of the diluent. The talc identified by Riggs as Cyprus BT-200 is now called Silverline 002 by Luzenac Americas, Inc. The PDIS content, that is diluent content, of the resultant potato seed piece treatment fungicide dust ranged from 89.5% to 94.7% w/w (weight percent). While Riggs may have successfully included alder bark in the diluent, as aforementioned the use of alder bark is not as efficacious as desired, due to cost, limited supply and because it does not effectively reduce fugitive dust, among other reasons.

SUMMARY OF THE INVENTION

Incorporating organic matter, preferably from oilseed hulls and thereby having elevated oil content, and most preferably from ground powdered sunflower seed hulls, into powdered materials greatly reduces generation of fugitive dust. Generally, manufacturing, handling and use of powder materials generates airborne fugitive dust posing health risks to those in proximity due to inhalation of the fine dust particles which may also contain health hazardous active ingredients. In addition to inhalation, skin contact with active ingredients in powder materials can also be hazardous. Fugitive dust has also been known to create conditions conducive to explosions. The use of ground or powdered sunflower seed hulls as a carrier and/or diluent makes beneficial and productive use of an organic residue which is a byproduct of other industries. By incorporating powdered organic residues, preferably from oilseed hulls and most preferably from ground or powdered oilseed sunflower seed hulls, into powder compositions, fugitive dust is greatly reduced if not eliminated.

In a first manifestation, the invention is a method of treating potato seed pieces with an oil-bearing organic containing composition. According to the method, the oil-bearing organic is dried and reduced to an oil-bearing powder having microscopic frayed ends. The oil-bearing organic is incorporated with an active biocidal ingredient to produce a potato treating composition. Potato seed pieces are coated with the potato treating composition, and then the coated potato seed pieces are suberized to yield suberized potato seed pieces. The suberized potato seed pieces are planted.

In a second manifestation, the invention is a powdered potato treatment composition, comprising an active biocidal ingredient and a powdered oilseed residue carrier.

OBJECTS OF THE INVENTION

A first object of the invention is to provide a commercially viable potato treatment composition and method. A second object of the invention is to provide such a composition which will adhere to the cut surface of a tuber, but which will not clump prior to application to the cut surface. Another object of the present invention is to reduce the generation of fugitive dust, and thereby improve the coating efficacy while also enhancing worker and product safety. A further object of the invention is to absorb moisture from the cut surface of a tuber, while not undesirably adsorbing moisture from the air. Yet another object of the present invention is to provide a diluent having a small particle size, with improved flowability. An additional object of the invention is to provide a composition which has a lower bulk density, in turn enabling a given product weight to treat a greater surface area. A further object of the invention is the provision of a potato treatment whose performance is relatively independent of geographic region and such factors as humidity.

DESCRIPTION OF THE PREFERRED EMBODIMENT

The most preferred embodiment of the present invention is a potato treatment composition and method which assists in the suberization process. In accord with the preferred embodiment, a potato treatment composition incorporates organic material, which may be derived from organic waste or residue, preferably from oilseed hulls and most preferably from ground or powdered oilseed sunflower seed hulls, into powder compositions.

The oilseed hulls which are suitable for use in the present invention are most preferably those which will greatly reduce or eliminate generation of fugitive dust. Powder material manufacture, handling and use commonly generates fugitive dust which causes environmental contamination posing health risks to those in proximity of the fugitive dust, particularly when the powder material comprises harmful active ingredients. Fugitive dust may include active ingredients including herbicides, insecticides, fungicides, other pesticides, pigments or other active substances. The active ingredient can be impregnated in or on a carrier or incorporated with diluent materials, yet the combination may still cause fugitive dust. By incorporating organic residue, preferably ground or powdered sunflower seed hulls, into a potato treatment composition, dust is greatly reduced. Additional benefits are also obtained, some which will be discussed in greater detail herein below. One particularly noteworthy benefit of the preferred oil seed hulls is reduced density. Another is an unexpected decrease in shrinkage during suberization.

A diluent comprising sunflower seed hulls is preferable to related art diluents since ground or powdered sunflower seed hulls reduce fugitive dust and provide additional benefits, while utilizing what is typically viewed as a waste product. Discarded oilseed hulls, most preferably sunflower seed hulls, which are otherwise of little or no economic value have surprising and unexpected benefit in reducing harmful airborne dust. A preferred sunflower seed hull is that of the species Helianthus annuus, family Asteraceae, the common edible sunflower seed. Sunflower seeds are shelled for producing edible sunflower seeds and for producing sunflower oil. By using the sunflower seed hulls in another industry for fugitive dust control the hulls become a useful co-product.

The term organic residue is hereby defined as a byproduct of an organic matter process. While not wishing to be limited by theory, and recognizing the benefits and advantages specifically in oilseed sunflower seed hulls, it is contemplated herein that other oil-bearing organic materials may also provide the desired benefits, provided there is sufficient oil and a frayed edge, as will be described herein below.

For example, when soybeans are processed to make tofu or soymilk, the soybean pod is left behind in the field and the coating on the soybean is removed during the process of making tofu or soymilk. The coating becomes a useful organic residue analogous to the sunflower seed hull. The coating is often dried and ground, particularly for use in livestock feed. It is believed the soybean coating as a powder would contain minute, frayed shreds, and during processing might either intrinsically or through processing or additives, provide a residual organic oil within the fibers, similar to sunflower seed hulls. Other oil crops which may contain a sufficient oil content, which may for exemplary purposes only vary between approximately 3 and 20 weight percent, and for which organic residues may be useful for carrier or diluent purposes include, but are not restricted to, rapeseed, mustard, safflower, crambe, sesame, olive, coconut, and palm. Higher oil content organic materials have been determined to provide substantial benefit and advantage over those of lower oil content, and the determination of what type of oil and substrate are suitable to achieve the present benefits will be apparent to those skilled in the art after a review of the present specification.

In some seed hulls and residues, the oil content has been determined to be relatively insufficient for preferred operation of a suitable diluent. As one example, the efficacy of confectionary sunflower hulls, which have a substantially lower oil content than that found in oil-seed sunflower hulls, the generation of fugitive dust is substantially greater. This is illustrated in the following example. As is evident, the high-oil sunflower seed hulls outperformed the other common diluents by a large margin.

Example I

Test samples were prepared by oven-drying sunflower seed hulls at 50 degrees C. The hulls were then ground to pass a 20 mesh screen in a Thomas-Wiley Mill. They were further reduced to a powder in a ball mill for 12 hours. The powdered sunflower hulls with samples of other common diluent ingredients were tested for dustiness analysis performed according to methods described in Gill et al. (1997). In summary, the dustiness of several standard dry diluent materials was evaluated by weighing the diluent and then tumbling the material in a rotating drum. Dust generated from the tumbling was measured by drawing through a filter and weighing. The results of the analysis are shown in FIG. 2 as the mean of three replications and expressed as milligrams of dust generated from five grams of sample. The lower the value of "milligrams per five gram sample", the lower the amount of dust. Results demonstrate that powdered sunflower oilseed hulls create minimal to virtually no dust while all other materials tested produce a substantial amount of nuisance dust.

| Material | Description | mg/5 g | Std. dev. |
|---|---|---|---|
| Talc | Luzenac Silverline 002 | 29.418 | 2.75 |
| Zeolite | Teague Mineral Products CH | 50.172 | 1.25 |
| Bark flour | MODAL alder bark flour | 28.419 | 0.58 |
| 10010 wood flour | American Wood Fibers maple | 5.531 | 1.27 |
| 8010 wood flour | American Wood Fibers maple | 5.784 | 0.41 |
| Sunflower hull (confectionary, non-oilseed) | Sigco Sun, 5.65% fat/oil | 3.947 | 0.57 |
| Sunflower hull (oilseed variety) | Dahlgren, 10.68% fat/oil | 0.008 | 0.01 |

Particularly noteworthy is the nearly 4,000 fold decrease in the amount of dust produced by high oil sunflower hull when compared to alder bark.

Generally, sunflower seeds are hulled prior to oil extraction. However, the sunflower oil industry is also known to grind the sunflower kernel within the hull, extracting oil from both kernel and hull at the same time. The material contains preferably about 5 to 15 weight percent oil, and more broadly 3 to 20 weight percent oil. The organic residue is a combination of ground kernel and hull. It is appreciated that an effective carrier or diluent could be made from such an organic residue. The present inventor discovered that ground or powdered sunflower seed hulls is an effective carrier and/or diluent for reducing dust and for diluting active ingredients. The ground or powdered sunflower seed hulls are believed to be an effective carrier and diluent due not only to the inherent high oil content (about 3 to 20 weight percent) but also to the shape of the ground or powdered seed hulls which helps physically hold onto small particles. The sunflower seed hulls, when ground or powdered, shred into small or minute irregular shaped organic fibers with frayed ends. Even in powder form, the sunflower seed hulls appear shredded in microscopic view. Existing known diluent powders are less than approximately 50 to 500 microns. A human hair is about 25 microns and respirable dust is about 10 microns or less. Here, the sunflower seed hulls are ground or powdered to 100 to 200 microns or less with some particles as small as 5 microns, yet the material still traps fugitive dust without the hull material itself creating appreciable fugitive dust.

Example II

Currently, talc and powdered alder bark are the primary carrier and diluent ingredients used in potato fungicide dusts, as illustrated by the following table, which illustrates a potato dust inert system from U.S. Pat. No. 6,228,883.

| Ingredient | % (w/w) |
|---|---|
| Talc | 48.39 |
| Zeolite | 16.12 |
| Alder bark | 35.49 |

Neither talc nor alder bark is an effective dust control agent, as evidenced from Example I above. Furthermore, as the supply of alder bark dwindles relative to demand, new ingredients are needed. Sunflower seed hulls are plentiful and are viewed as a waste product of industry. Thus, they are an ideal source which is replenishable with yearly sunflower harvests.

The preferred method for preparing powdered sunflower seed hulls in accord with the present invention comprises drying the sunflower seed hulls in an oven, grinding the hulls, screening the hulls to pass through a mesh screen, and milling the hulls in a ball mill or other suitable apparatus. Those skilled in the art will recognize that the grinding and milling steps are each capable of producing both particle size reduction and the preferred fibrous cut ends, and so a variety of sequences may be selected depending upon the particular equipment and processing time available. Grinding and/or milling might, for exemplary purposes and not limited thereto, be accomplished with a hammermill, pulverizer, or disc refiner, and sifting or screening could occur at suitable points in the operation. The drying step preferably is at a temperature less than the volatilization temperature of the organic residue oil and less than deterioration temperature of the sunflower seed hulls or other carrier or diluent material being simultaneously dried, generally about 35 to 55° C. (about 95 to 130° F.). On a large scale, the sunflower seed hulls might for exemplary purposes be dried in a fluidized bed or other large scale dryer.

In accord with the present invention, the preferred method for treating potatoes first comprises preparing powdered sunflower seed hulls as described herein above. The method for treating potatoes further includes incorporating the powdered sunflower seed hulls with other materials such as a powdered active ingredient or diluent. Alternatively, mixing the sunflower seed hulls and active ingredient with or without a diluent or carrier may occur prior to grinding or powdering the resultant mixture.

Example III

An improved fungicide powder for potato seed treatment in dry climates comprises, talc at 44%, zeolite at 24%, wood flour at 12% (maple flour), powdered sunflower seed hull at 12% and Dithane® M-4.5 at 8%, each by weight percentages. Dithane® M-45 is a fungicide generically called mancozeb by Dow AgroSciences. The amounts of powdered sunflower seed hull increase from 10 to 25 percent with decreasing zeolite, wood flour and talc. Generally for potato seed treatments, the sunflower seed hulls comprise about 10 to 45%, wood flour ranges from about 5 to 50%, and the active ingredient ranges from about 1 to 20 weight percent, with a balance of other diluent materials. The percentage of sunflower seed hull is most preferably great enough to reduce fugitive dust yet not so great as to clump during use.

Example IV

A base set of ingredients used to prepare five experimental formulations for fungicide powder for potato seed treatment based on maple wood flour and powdered sunflower seed hulls was prepared. The base ingredients included talc at 43.9%, zeolite at 24.3%, and Dithane® (mancozeb, Dow AgroSciences) at 7.45%, each by weight. The remaining 24.3% by weight was selected in accord with each of the following five examples.

Example V

A first experimental formulation, F1, was prepared using the results of example IV, and further including maple flour at 24.3%.

Example VI

A second experimental formulation, F2, was prepared using the results of example IV, and further including maple flour at 18.2% and sunflower hulls at 6.1%.

Example VII

A third experimental formulation, F3, was prepared using the results of example IV, and further including maple flour at 12.2% and sunflower hulls at 12.2%.

Example VIII

A fourth experimental formulation, F4, was prepared using the results of example IV, and further including maple flour at 6.1% and sunflower hulls at 18.2%.

Example IX

A fifth experimental formulation, F5, was prepared using the results of example IV, and further including sunflower hulls at 24.3%.

The five experimental formulations F1-F5, prepared in Examples V-IX above, were then compared with "TOPS MZ," a disclosed formulation in Chollet '953 and a standard commercial fungicide dust product, at three different geographic locations. Example show the results of the five experimental formulations and the known formulation at three different locations.

Example X

Effect of seed treatment product or formulation on performance of Russet Norkotah at the Klamath Experiment Station, Klamath Falls, Oreg.

| Treatment | No. 1s 4-8 oz | No. 1s 8-12 oz | No. 1s >12 oz | No. 1s Total cwt/acre | Bs | No. 2s | Cults | Total Yield |
|---|---|---|---|---|---|---|---|---|
| F1 | 76 | 110 | 193 | 379 | 19 | 33 | 22 | 453 |
| F2 | 98 | 121 | 193 | 412 | 15 | 36 | 18 | 481 |
| F3 | 95 | 124 | 171 | 390 | 20 | 32 | 16 | 458 |
| F4 | 88 | 106 | 182 | 376 | 14 | 50 | 17 | 457 |
| F5 | 91 | 138 | 218 | 394 | 15 | 41 | 15 | 465 |
| Tops MZ | 93 | 123 | 166 | 382 | 20 | 47 | 20 | 469 |
| Mean | 90 | 122 | 184 | 396 | 17 | 39 | 18 | 471 |
| CV(%) | 17 | 19 | 24 | 12 | 33 | 33 | 57 | 10 |
| LSD (0.05) | NS | NS | NS | NS | NS | NS | NS | NS |

Example XI

Effect of seed treatment product or formulation on performance of Russet Norkotah at the Central Oregon Agricultural Research Center, Madras, Oreg.

| Treatment | <4 oz | No. 1s 4-12 oz | No. 1s >12 oz | No. 1s Total cwt/acre | Culls | Total Yield | Stem/ Plant | Emerg. 28 DAP |
|---|---|---|---|---|---|---|---|---|
| F1 | 27 | 140 | 296 | 436 | 110 | 575 | 2.4 | 97 |
| F2 | 19 | 142 | 335 | 474 | 118 | 619 | 2.1 | 94 |
| F3 | 22 | 187 | 331 | 518 | 71 | 611 | 2.3 | 97 |
| F4 | 22 | 194 | 289 | 484 | 116 | 621 | 2.3 | 91 |
| F5 | 22 | 184 | 307 | 490 | 70 | 582 | 2.3 | 94 |
| Evolve | 24 | 158 | 371 | 529 | 109 | 665 | 2.3 | 94 |
| Tops | 25 | 178 | 207 | 385 | 85 | 494 | 2.4 | 97 |
| Mean | 23 | 174 | 302 | 476 | 89 | 590 | 2.3 | 96 |
| CV(%) | 28 | 29 | 24 | 17 | 50 | 10 | 12 | 5 |
| LSD (0.05) | NS | NS | 108 | 118 | 65 | 88 | NS | NS |

Example XII

Effect of seed treatment product or formulation on performance of Russet Norkotah at the Malheur Experiment Station, Ontario, Oreg., 2005

| Treatment | No. 1s 4-6 oz | No. 1s 6-12 oz | No. 1s >12 oz | No. 1s Total cwt/acre | Bs | No. 2s | Cults | Total Yield |
|---|---|---|---|---|---|---|---|---|
| F1 | 90 | 202 | 26 | 318 | 76 | 54 | 5 | 452 |
| F2 | 84 | 219 | 25 | 328 | 75 | 63 | 0 | 466 |
| F3 | 92 | 206 | 27 | 325 | 71 | 55 | 4 | 456 |
| F4 | 85 | 177 | 24 | 285 | 71 | 64 | 1 | 420 |
| F5 | 76 | 218 | 54 | 347 | 60 | 63 | 0 | 471 |
| Tops MZ-G | 85 | 205 | 30 | 320 | 76 | 64 | 1 | 461 |
| Mean | 85 | 204 | 29 | 318 | 72 | 61 | 2 | 453 |
| CV(%) | 57 | 21 | 68 | 15 | 19 | 30 | 338 | 8 |
| LSD (0.05) | NS | NS | NS | NS | NS | NS | NS | NS |

From examples X-X11 it is apparent that the experimental formulations F1-F5 performed quite comparably to the known formulation. The dust reduction quality of powdered oilseed residue, particularly ground or powdered sunflower seed hulls when properly formulated, will greatly reduce undesirable fugitive dust, while providing particular benefit to the potato industry. Two additional and unexpected benefits occurred in some of the experimental formulations. First of all, the experimental fungicide powder formulations with powdered sunflower seed hulls did not tend to clump as compared to known fungicide dusts. Secondly, the potato seed pieces did not tend to shrink due to moisture depletion as is known to occur with known fungicide dusts.

The invention is discussed by example throughout the written description and drawings. It should be understood that variations are possible while adhering to the inventive concept. Such variations are contemplated as being a part of the present invention. As but one example, it is further contemplated herein to incorporate the addition of oil when grinding or milling dry or non-oil bearing organic residue, with the intent to increase the weight percentage of oil. For the purposes of the present disclosure, dry or non-oil bearing organic residue will be understood to be organic residue which performs comparably to wood flower, as opposed to the oilseed sunflower seed hulls in the most preferred embodiment. This incorporation of oil is preferably optional only when working with organic materials which will continue to mill or grind properly in the presence of the additional oil, to most preferably produce fibrous cut ends while still impregnating with oil. In such case, the particular milling method or technique may be vital to the finished product, and appropriate consideration will be given thereto. More particularly, ball milling and similar processes are known to provide a large number of compressions, which for some resilient and porous substrates will result in absorption of oil into the substrate during milling. Consequently, the addition of a suitable substrate, an oil additive, and suitable ball milling is anticipated as one avenue to provide benefits commensurate with the most preferred oilseed sunflower hulls described herein above with only reasonable experimentation and with the teachings of the present invention. While oilseed sunflower seed hulls possess the desired characteristics with the foregoing processing, those skilled in the art will with these present teachings and reasonable experimentation thereby recognize other suitable compositions and processing techniques.

Therefore, while the foregoing details what is felt to be the preferred embodiment of the invention, no material limitations to the scope of the claimed invention are intended. Further, features and design alternatives that would be obvious to one of ordinary skill in the art are considered to be incorporated herein. The scope of the invention is set forth and particularly described in the claims herein below.

I claim:

1. A method of treating potato seed pieces with an oil-bearing organic containing composition, comprising the steps of:
   drying said oil-bearing organic;
   reducing said oil-bearing organic to an oil-bearing powder having microscopic frayed ends;
   incorporating said oil-bearing organic with an active biocidal ingredient to produce a potato treating composition comprising 10-45% sunflower seed hulls, 5-50% wood flour, and 1-20% active ingredient, each by weight percent;
   coating said potato seed pieces with said potato treating composition;
   suberizing said coated potato seed pieces to yield suberized potato seed pieces; and
   planting said suberized potato seed pieces.

2. The method of treating potato seed pieces with an oil-bearing organic containing composition of claim 1, wherein said oil-bearing organic comprises oilseed sunflower seed hulls.

3. The method of treating potato seed pieces with an oil-bearing organic containing composition of claim 1, wherein said oil-bearing organic is an organic residue from an oilseed crop containing 3 to 20 weight percent oil.

4. The method of treating potato seed pieces with an oil-bearing organic containing composition of claim 1, further comprising the step of screening said oil-bearing organic through a mesh screen.

5. The method of treating potato seed pieces with an oil-bearing organic containing composition of claim 1, further comprising the step of milling said hulls in a ball mill.

6. A powdered potato treatment composition, comprising:
   an active biocidal ingredient; and
   a powdered oilseed residue carrier comprising oilseed sunflower seed hulls.

7. The powdered potato treatment composition of claim 6, wherein said oilseed sunflower seed hulls are from the species *Helianthus annuus*, family Asteraceae.

8. The powdered potato treatment composition of claim 6, wherein said oilseed sunflower seed hulls are ground to 100 to 200 microns or less, and have microscopic frayed ends.

9. The powdered potato treatment composition of claim 6, further comprising 10-45% sunflower seed hulls, 5-50% wood flour, and 1-20% active biocidal ingredient, each by weight percent.

10. The powdered potato treatment composition of claim 6, wherein said powdered oilseed residue carrier comprises ground or powdered organic material having frayed fibers and oil for trapping said fugitive dust.

11. A method of treating potato seed pieces with a sunflower seed hulls containing composition, comprising the steps of:
    drying said sunflower seed hulls;
    reducing said sunflower seed hulls to an oil-bearing powder having microscopic frayed ends;
    incorporating said oil-bearing powder with an active biocidal ingredient to produce a potato treating composition;
    coating said potato seed pieces with said potato treating composition;
    suberizing said coated potato seed pieces to yield suberized potato seed pieces; and
    planting said suberized potato seed pieces.

* * * * *